(12) United States Patent
Bading et al.

(10) Patent No.: US 8,969,671 B2
(45) Date of Patent: Mar. 3, 2015

(54) PLANTS AND SEEDS OF SORGHUM VARIETY GSV415986

(71) Applicant: Monsanto Technology LLC, St. Louis, MO (US)

(72) Inventors: Ryan S. Bading, Corpus Christi, TX (US); Miguel A. Gutierrez, O'Fallon, MO (US); Michael C. Lenz, Wichita, KS (US)

(73) Assignee: Monsanto Technology LLC, St. Louis, MO (US)

( * ) Notice: Subject to any disclaimer, the term of this patent is extended or adjusted under 35 U.S.C. 154(b) by 137 days.

(21) Appl. No.: 13/756,521

(22) Filed: Jan. 31, 2013

(65) Prior Publication Data

US 2014/0215648 A1    Jul. 31, 2014

(51) Int. Cl.
*A01H 5/00* (2006.01)
*C12N 15/82* (2006.01)
*A01H 5/10* (2006.01)

(52) U.S. Cl.
CPC ............. *A01H 5/10* (2013.01); *C12N 15/8245* (2013.01); *C12N 15/8251* (2013.01); *C12N 15/8274* (2013.01); *C12N 15/8275* (2013.01); *C12N 15/8278* (2013.01); *C12N 15/8279* (2013.01); *C12N 15/8286* (2013.01); *C12N 15/8289* (2013.01)
USPC ............ 800/320; 800/260; 800/278; 435/410

(58) Field of Classification Search
USPC ........................................................ 800/320
See application file for complete search history.

(56) References Cited

U.S. PATENT DOCUMENTS 5,523,520 A     6/1996  Hunsperger et al.
8,461,426 B2 *  6/2013  Bading et al. ................. 800/320

OTHER PUBLICATIONS

House, "A Guide to Breeding Sorghum," ICRISAT, Andhra Pradesh India pp. 27-149, 1985.
Allard, In: Principles of Plant Breeding, Chapter 6 through Chapter 9, University of California, Davis, California, John Wiley & Sons, New York, pp. 50-98, 1960.
Eshed et al., "Less-than-additive epistatic interactions of quantitative trait loci in tomato," *Genetics*, 143:1807-1817, 1996.
Fehr (ed.), In: Principles of Cultivar Development, vol. 1: Theory and Technique, pp. 360-376, 1987.
Kraft et al., "Linkage disequilibrium and fingerprinting in sugar beet," *Theor Appl Genet*, 101:323-326, 2000.
Poehlman, J.M. and Sleper, D.A., "Methods in Plant Breeding," In Breeding Field Crops, 4th ed., *Iowa State Press*, pp. 159-239, 1995.
Kresovich, S. et al., "Application of Cell and Tissue Culture Techniques for the Genetic Improvement of Sorghum" Advances in Agronomy, vol. 41, pp. 147-170 (1987).
Tomes, D.T., "Cereal Tissue & Cell Culture", Chapter 6, pp. 176-203. Martinus Hijnoff/Dr. W. Juns. Amtisdau, Bright & Jones (ed.) 1985.
Vanderlip, R.L., "How a Sorghum Plant Develops", Kansas State University Agricultural Experiment Station and Cooperative Extension Service, S-3 Jan. 1993 [online], http://www.ksre.ksu.edu/bookstore/pubs/s3.pdf.
Variety specific information as indicated in transmittal letter of Nov. 18, 2013 Information Disclosure Statement for U.S. Appl. No. 13/756,521.

* cited by examiner

*Primary Examiner* — Li Zheng
(74) *Attorney, Agent, or Firm* — Dentons US LLP

(57) ABSTRACT

The invention relates to the *sorghum* variety designated GSV415986. Provided by the invention are the seeds, plants and derivatives of the *sorghum* variety GSV415986. Also provided by the invention are tissue cultures of the *sorghum* variety GSV415986 and the plants regenerated therefrom. Still further provided by the invention are methods for producing *sorghum* plants by crossing the *sorghum* variety GSV415986 with itself or another *sorghum* variety and plants produced by such methods.

20 Claims, No Drawings

PLANTS AND SEEDS OF SORGHUM VARIETY GSV415986

BACKGROUND OF THE INVENTION

Field of the Invention

The present invention relates generally to a new *sorghum* line, designated GSV415986, as well as to seed, plants, cultivars, and hybrids related thereto. The invention also relates to methods for producing *sorghum* seeds and plants from GSV415986.

SUMMARY OF THE INVENTION

In an embodiment, the invention is directed to a seed or plant of *sorghum* variety GSV415986. The invention also relates, in an embodiment, to a method of producing a plant of variety GSV415986 comprising an added desired trait, the method comprising introducing a transgene conferring the desired trait into a plant of variety GSV415986.

Other methods embodied in the invention include a method of introducing a single locus conversion into variety GSV415986 comprising: crossing a plant of variety GSV415986, with a second plant comprising a desired single locus to produce $F_1$ progeny plants; selecting one or more $F_1$ progeny plants that have the single locus; crossing the one or more selected $F_1$ progeny plants with at least a first plant of variety GSV415986 to produce backcross progeny plants; selecting backcross progeny plants that have the single locus and essentially all of the physiological and morphological characteristics of variety GSV415986 listed in Table 1; and repeating the crossing of the one or more selected $F_1$ progeny plants step and the selecting of backcross progeny plants step one or more times in succession to produce selected second or higher backcross progeny plants that comprise the single locus and essentially all of the physiological and morphological characteristics of variety GSV415986 listed in Table 1.

Still further, in an embodiment, the invention relates to a method of producing an inbred plant derived from the variety GSV415986, the method comprising the steps of: preparing a progeny plant derived from variety GSV415986, by crossing a plant of the variety GSV415986 with a plant of a second variety; crossing the progeny plant with itself or a second plant to produce a seed of a progeny plant of a subsequent generation; growing a progeny plant of a subsequent generation from said seed and crossing the progeny plant of a subsequent generation with itself or a second plant; and repeating the crossing step and the growing step for an additional three or more generations with sufficient inbreeding to produce an inbred plant derived from the variety GSV415986.

DETAILED DESCRIPTION OF THE INVENTION

The following definitions apply to the terms used herein:

The characteristic level of a trait that is presented as a rating is indicated or measured using the following 1 through 9 rating scale: 1 to 2 indicates excellent, 3 to 4 indicates very good, 5 to 6 indicates good, 7 to 8 indicates fair, and 9 indicates poor. This scale is used for all traits unless specifically indicated otherwise.

Agronomic Rating. Agronomic rating is a composite rating where consideration is given to all agronomic characteristics that are in evidence at the location where the rating is made.

Allele. An allele is a variant of a DNA sequence at a given locus.

Alter. The term alter or alteration refers to the utilization of up-regulation, down-regulation, or gene silencing.

Anther Color. Anther color is a description of the color of the anthers on the day they are shedding pollen. The color is generally described as yellow, red, or mottled but other colors and descriptions are possible.

Anthocyanin Presence. Anthocyanin presence will be indicated by purple or red coloration in the stalk and leaves, particularly where damage to tissue has occurred. Anthocyanin presence is indicated as present or not present.

Awns. Awns are bristles arising from a spikelet part. Some lines have a very small awn, called a tip awn. Awn presence is indicated as present or not present.

Backcrossing. Backcrossing is a process in which a breeder repeatedly crosses hybrid progeny back to one of the parents. For example, a first generation hybrid $F_1$ may be crossed with one of the parental genotypes of the $F_1$ hybrid.

Barren Plants. Plants that are barren are those that lack a head with grain or that have only a few seeds.

Bloom 10%. Bloom 10% refers to the number of days from planting to when a line in a nursery row or field has completed 10% of the blooming process.

Bloom 50%. Bloom 50% refers to the number of days from planting to when a line in a nursery row or field has completed 50% of the blooming process.

Bloom 90%. Bloom 90% refers to the number of days from planting to when a line in a nursery row or field has completed 90% of the blooming process.

Cell. Cell, as used herein, includes a plant cell, whether isolated, in tissue culture, or incorporated into a plant or plant part.

Charcoal Rot Resistance. Charcoal rot resistance refers to a visual rating of a variety's resistance to Charcoal Rot disease.

Chinch Bug Resistance. Chinch bug resistance refers to a visual rating of the *sorghum* plant's ability to grow normally when infested with a large number of chinch bugs.

Color Intensity Score. Color Intensity score is a rating of the intensity and brightness of color for a particular variety.

Days to Flower. Days to flower refers to the predicted number of days, measured from the time of planting, required for flowers of a variety to bloom. Days to flower for the same variety may vary depending on the environment in which it is grown.

Days to Harvest. Days to harvest refers to the predicted number of days, measured from the time of planting, required for a variety to be ready for harvest. Days to harvest for the same variety may vary depending on the environment in which it is grown.

Downy Mildew Resistance. Downy mildew resistance refers to a visual rating of a variety's resistance to races 1, 3, and/or 6 of Downy Mildew, a fungal disease that infects *sorghum* plants.

Endosperm Color. Endosperm color is described as white or yellow.

Endosperm Texture. Endosperm Texture is described as vitreous, floury, or intermediate.

Elite *Sorghum* Hybrid. An elite *sorghum* hybrid is a *sorghum* hybrid which has been sold commercially.

Elite *Sorghum* Parent Line. An elite *sorghum* line is a *sorghum* line which is the parent line of a *sorghum* hybrid which has been sold commercially.

Embryo. The embryo is the small plant contained within a mature seed.

Essentially all of the physiological and morphological characteristics. This phrase refers to a plant having essentially all of the physiological and morphological characteristics of the referenced plant or variety, as determined at a 5% significance level for quantitative data.

*Fusarium* Head Blight Resistance*. *Fusarium* Head Blight Resistance refers to a visual rating of a variety's resistance to *Fusarium* Head Blight disease, which is caused by *Fusarium moniliforme* Sheld.

Gene. As used herein, gene refers to a segment of nucleic acid. A gene can be introduced into a genome of a species, whether from a different species or from the same species, using transformation or various breeding methods.

Genetic Complement. The phrase genetic complement is used to refer to the aggregate of nucleotide sequences, the expression of which sequences defines the phenotype of a plant, or a cell or tissue of that plant.

Gene Silencing. Gene silencing means the interruption or suppression of the expression of a gene at the level of transcription or translation.

Genotype. Genotype refers to the genetic constitution of a cell or organism.

Glume Color. The glume refers to one of a pair of empty scales at the base of a spikelet. Glume color is described as tan, mahogany, red, purple, or black.

Grain Set Under Bags. Grain set under bags is a measure of the self fertility of a plant. Pollinating bags are placed over the panicle prior to the initiation of flowering and remain in place until seed set can be determined, generally three weeks or more after flowering has been completed. At that time a percentage rating of seed set is made. This can range from 0% (indicating the plant is pollen sterile) to 100% (indicating full pollen fertility). Intermediate ratings can indicate varying levels of partial fertility.

Grain Weathering Resistance. Grain weathering resistance refers to a visual rating of how well the exposed grains in the *sorghum* head are able to retain normal seed quality when exposed to normal weather hazards and surface molds.

Greenbug Resistance. Greenbug resistance refers to a visual rating of a varieties resistance to one or more biotypes of the greenbug insect pest. Resistance to a particular biotype is indicated by "E" (Biotype E) and/or "I" (Biotype I).

Head Smut Resistance. Head smut resistance refers to a visual rating of a variety's resistance to this fungal disease that infects *sorghum* plants. The rating is based on the percentage of smut-infected plants.

Height Uniformity. Height uniformity is a rating of the uniformity of the height of all of the main heads and tillers for a variety.

Leaf Attitude. Leaf attitude refers to an indicator of the attitude of the leaves with reference to the stalk, where "E" indicates erect (leaf angle [panicle to leaf axil to leaf midrib] less than about 45 degrees), "SE" indicates semi-erect (leaf angle of about 45-80 degrees), and "H" indicates horizontal (leaf angle of about 80 degrees or greater).

Leaf Color Intensity. The leaf color intensity is described as the color intensity from very light to very dark.

Leaf Length and Width. Leaf length and width is measured by selecting the largest leaf, after flowering, on a representative sample of plants and measuring the maximum length and width in inches. Generally, this will be a leaf towards the middle of the plant.

Leaf Number. Leaf number is measured by counting the total number of leaves on the plant after flowering. Some of the first leaves may have deteriorated by that time, so an estimate can be made.

Locus. A locus is the specific location of a gene or DNA sequence on a chromosome.

Maturity. The maturity of a variety is measured as the number of days between planting and physiological maturity.

Maize Dwarf Mosaic Virus (MDMV). MDMV refers to a visual rating of a variety's resistance to the Maize Dwarf Mosaic Virus, type "A."

Mid-Rib Color. Mid-rib color can be described as white, cloudy, intermediate, or brown. White indicates a dry mid-rib and stalk, while cloudy indicates that they are juicy. Brown indicates the presence of a mutant allele that conditions for a reduced amount of lignin in the plant.

Panicle Appearance Rating. Panicle Appearance Rating is a rating of the overall panicle appearance that includes panicle type, panicle length, panicle diameter, grain color, grain color intensity, grain weathering, seed size, glume size, presence or absence of panicle diseases (i.e. *fusarium* head blight), and other criteria that may be important for a given environment.

Panicle Branch Attitude. Panicle branch attitude is an indicator of the attitude of the panicle branch with reference to the stalk, where "E" indicates erect (panicle branch angle [central rachis to panicle branch axil to panicle branch] less than about 45 degrees), "SE" indicates semi-erect (panicle branch angle of about 45-80 degrees), and "H" indicates horizontal (panicle branch angle of about 80 degrees or greater).

Panicle Blasting Percent. Panicle blasting percent is the percentage of florets in a panicle aborted by a *sorghum* plant. This data is usually recorded on cytoplasmic male sterile lines and is influenced by genotype and environment. Presence of this condition is a deleterious trait for commercial seed production.

Panicle Branch Length. Panicle Branch Length is measured by selecting panicle branches from the middle of the panicle, which are generally the longest, and measuring the length in inches.

Panicle Diameter. Panicle Branch Diameter is a measurement, in inches, of the largest part of the panicle at the stage when grain is fully mature.

Panicle (or Head) Exsertion. Panicle (or Head) Exsertion is a 1 to 9 rating representing the length of the peduncle exposed between the base of the panicle (head) and the flag leaf of the plant. A high score indicates more distance between the flag leaf and the *sorghum* head, while a low score indicates a short distance between the two.

Panicle Length. Panicle length is the length of the panicle, in inches, from the attachment point of the lowest branch to the tip of the uppermost branch in its normal orientation.

Panicle (or Head) Type. Panicle (or Head) Type is an indicator of the morphology of a *sorghum* plant's head (panicle), where "O" indicates an open panicle characterized by either more distance between the panicle branches or longer panicle branches; "SO" indicates a less open panicle; "SC" indicates a semi-compact panicle caused by shorter panicle branches arranged more closely on the central rachis; and "C" indicates a very compact panicle caused by very short panicle branches arranged tightly on the central rachis.

Panicle Shape. Panicle shape is an indicator of the shape of a *sorghum* plant's head (panicle), where "C" indicates cylindrical, "E" indicates elliptical, "O" indicates oval, and "R" indicates round.

Plant. As used herein, the term plant includes reference to an immature or mature whole plant, including a plant from which seed or grain or anthers have been removed.

Plant Color. Plant color results from the presence or absence of anthocyanin pigments in the stalks and other organs of *sorghum* plants. The type and degree of coloration is determined by genotype and is somewhat subject to growing conditions, but varieties typically show varying degrees of coloration ranging from: absent (tan plant) to very strong (deep purple coloration). Ratings generally are tan, red, or purple.

Plant Height. Plant height refers to the average height of the plant at the end of flowering, assuming the plant is not lodged. This varies from variety to variety and although it can be influenced by environment, relative comparisons between varieties grown side by side are useful for variety identification. Plant height is measured in inches, from the ground to the tip of the panicle.

Plant Parts. As used herein, the term plant parts (or "*sorghum* plant, or a part thereof") includes, but is not limited to, protoplasts, leaves, stalks, roots, root tips, anthers, stigmas, panicles, seeds, grains, embryos, pollen, ovules, flowers, shoots, tissue, cells, and meristematic cells.

Pollen Shed Rating. Pollen shed rating is a visual rating made during flowering indicating the amount of pollen shed, on a scale of 1 to 9, where 1 indicates heavy pollen shed and 9 indicates no pollen shed.

Pre-Flower Stress Tolerance. Pre-flower stress tolerance is a visual rating of the stress tolerance of a *sorghum* plant before flowering. Symptoms that indicate poor pre-flower stress tolerance include poor panicle exertion, delayed panicle development, panicle exsertion, and flowering, and in extreme cases, abortion of the panicle.

Post-Flower Stress Tolerance. Post-flower stress tolerance is a rating of the stress tolerance of a *sorghum* plant after flowering. Symptoms that indicate poor post-flower stress tolerance include varying degrees of senescence of leaves starting with the lower leaves, pre-disposition and infection by stalk rot organisms such as Charcoal Rot (*Macrophomina phaseolina*), and varying degrees of stalk lodging.

Post-Freeze Standability. Post-freeze standability is a rating of the standability of a *sorghum* plant after a freeze.

Regeneration. Regeneration refers to the development of a plant from tissue culture.

Relative Maturity. Relative maturity (RM) for a variety is based on the predicted number of days required for an inbred line or hybrid to reach the blooming stage from the time of planting. The RM rating is relative to a set of known check varieties and is determined using standard linear regression analysis.

Resistance to Lodging. Resistance to lodging is a visual rating (relative to check varieties) of a variety's ability to stand up in the field under high yield conditions and severe environmental factors. A variety can have good (remains upright), fair, or poor (falls over) resistance to lodging. The degree of resistance to lodging is not expressed under all conditions but is most meaningful when there is some degree of lodging in a field trial.

Root Lodging. Root lodging is the percentage of lodged plants of a variety caused by an inadequate root support system. If the stem of the plant leans at an angle of approximately 30 degrees or more from vertical, the plant is considered to be root lodged.

Seed Coat Color. The color of the seed coat can be variety-specific and can be red, brown, white, or yellow for inbred lines. For hybrids, the seed coat color may also be cream (from a white x yellow cross) and bronze (from a red x yellow cross).

Seeds per Pound. Seeds per pound refers to the number of seeds per pound of grain for a representative sample.

Seedling Vigor. Seedling vigor is a visual rating of the amount of vegetative growth. The rating is usually taken when the average entry in the trial is at the two- to three-leaf stage.

Selection Index. The selection index provides a single measure of a variety's performance based on a composite of multiple traits. A *sorghum* breeder may utilize his or her own set of traits for the selection index. Two of the traits usually included are yield and days to flower (relative maturity). The selection index data presented herein represent the mean values averaged across testing locations.

Single Gene Converted (Conversion). Single gene conversion or a single gene converted plant refers to plants that are developed by backcrossing, genetic engineering, or mutation, wherein essentially all of the desired morphological and physiological characteristics of a variety are recovered, in addition to the single gene transferred into the variety via the backcrossing technique, genetic engineering, or mutation.

*Sorghum* Midge Resistance. *Sorghum* Midge Resistance refers to a visual rating of a variety's resistance to *sorghum* midge, an insect pest that affects seed set by infecting the head.

Stalk Lodging. Stalk lodging refers to the percentage of lodged plants of a variety caused by stalks breaking above the ground due to natural causes.

Staygreen. Staygreen refers to a visual rating of a variety's ability to retain green leaf tissue. Ratings are most valuable in the presence of heat and/or drought stress during the grain fill period.

Testweight. Testweight is a measure of the weight (in pounds) of the grain harvested from a variety for a given volume (bushel), adjusted to a standard grain moisture content.

Threshability. Threshability refers to a visual rating (relative to check varieties) of the tendency of the seed of a variety to thresh free from the glumes.

Tillering. Tillering is a measure of the development of shoots from buds at the base of the main stem. This can be expressed as a visual rating (on a scale of 1 to 9, with 1 being a high degree of tillering and 9 being no tillering. This can also be expressed as an actual number of tillers per plant.

Tissue Culture. Tissue culture encompasses all cultural techniques in which a composition comprising embryonic issues, tissue fragments, calli, isolated cells or protoplasts of the same or a different type, or a collection of such cells are organized into a culture for the regeneration of functional plants or plant parts.

Yield. This term refers to the actual yield (measured in pounds per acre) of the grain harvested from a unit area for a variety, adjusted to a standard 13% grain moisture content.

Yield Under Stress. Yield under stress is a rating of the yield of grain harvested from a unit area when such unit area is under stress, for example, from drought or heat. This can be determined by comparing the points where regression lines intersect the y axis for different hybrids when yield for the individual hybrids is regressed against the average yield for all hybrids in the tests. A high value for y axis intercept indicates a drought and stress tolerant hybrid whereas a low value indicates poor drought and stress tolerance.

Reference now will be made in detail to the embodiments of the invention, one or more examples of which are set forth below. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Sorghum plants (*Sorghum bicolor* (L.) Moench) have both male (anthers) and female (stigma) reproductive parts located in the same flower in the panicle. Natural pollination occurs in sorghum when anthers shed pollen and pollen falls onto receptive stigmata. Because of the close proximity of the anthers and stigmata in the panicle, the rate of self pollination is very high (average 94%).

In an embodiment, the present invention relates to a *sorghum* plant of the variety designated GSV415986. The inbred *sorghum* plant variety designated GSV415986 was derived from an initial cross between the lines GSV420031 and GSV648384. The origin and breeding history of the *sorghum* variety designated GSV415986 can be summarized as follows:

Summer 1991 at Robstown, Tex. The inbred line GSV648384 (a proprietary Monsanto Company inbred) was crossed onto the inbred line GSV420031 (a proprietary Monsanto Company inbred) using a wet pollen emasculation in nursery rows 127 and 126 respectively, to produce an F1.

Winter 1992-1993 in Puerto Rico. The $F_1$ was grown and selfed using open pollination in nursery row PR2072 to produce F2 seed.

Summer 1993 at Robstown, Tex. The $F_2$ was grown in nursery row F2-11, it was selfed using open pollination, and the F3 selection was made. In this and in subsequent selection opportunities yield, stalk quality, root quality, disease tolerance, insect tolerance, plant height, head exsertion, and stress tolerance were some of the criteria used to determine which plants were selected.

Summer 1994 at Robstown, Tex. The F3 was grown in nursery row F3-76, it was selfed using open pollination, and the F4 selection was made.

Summer 1995 at Bishop, Tex. The F4 was grown in nursery row BA-80, it was bagged and self pollinated. Additionally the first cross of this line was made into sterile cytoplasm to develop an A-line (sterile female). The sterile cytoplasm donor was the inbred 82 and was grown in nursery row BA-74. A paired selection (the head from the B-line pollen donor, and the head from cytoplasm donor that was pollinated) of the F5 B-line and the MSC0 (male sterilization cross generation 0) A-line were harvested.

Winter 1995. The F5 B-line was grown in nursery row SANUR-333, and self pollinated, and the F6 B-line selection was made. The MSC0 A-line was not advanced in the winter nursery.

Summer 1996 at Bishop, Tex. The F6 B-line was grown in nursery row BCN-23 and self pollinated, and the F7 B-line selection was made. The MSC0 A-line was not advanced in the summer nursery.

During 1997 no advancements were made in either the B-line or the A-line.

Summer 1998 at Bishop, Tex. The F7 B-line was grown in nursery row AE-11. The MSC0 A-line (from 1995) was grown in nursery row AE-12. The B-line was self pollinated and the B-line was also crossed onto the A-line for the $1^{st}$ backcross into sterile cytoplasm. A paired selection was made and the F8 B-line and the MSC1 A-line were harvested.

Summer 1999 at Bishop, Tex. The F8 B-line was grown in nursery row AA-61. The MSC1 A-line was grown in nursery row AA-62. The B-line was self pollinated and the B-line was also crossed onto the A-line for the $2^{nd}$ backcross into sterile cytoplasm. A paired selection was made and the F9 B-line and the MSC2 A-line were harvested.

Summer 2000 at Bishop, Tex. The F9 B-line was grown in nursery row Nursery 3 HRR-47. The MSC2 A-line was grown in nursery row Nursery 3 HRR-48. The B-line was self pollinated and the B-line was also crossed onto the A-line for the $3^{rd}$ backcross into sterile cytoplasm. A paired selection was made and the F10 B-line and the MSC3 A-line were harvested.

Summer 2001 at Bishop, Tex. The F10 B-line was grown in nursery row Nursery 3 HRP-25. The MSC3 A-line was grown in nursery row Nursery 3 HRP-26. The B-line was self pollinated and the B-line was also crossed onto the A-line for the $4^{th}$ backcross into sterile cytoplasm. Bulk Flt B-line and bulk MSC4 A-line selections were harvested.

Summer 2002 at Plainview, Tex. The Flt B-line was grown in nursery row A1075. The MSC4 A-line was grown in nursery row A1076. The B-line was self pollinated and the B-line was also crossed onto the A-line for the $5^{th}$ backcross into sterile cytoplasm. A paired selection was made and the F12 B-line and the MSC5 A-line were harvested.

Summer 2003 at Plainview, Tex. The F12 B-line was grown in nursery rows G-583, 585, 587 & 589. The MSC5 A-line was grown in nursery rows G-584, 586, 588 & 590. Cross pollinations were made between the B-line & A-line paired rows (583 & 584, 585 & 586, 587 & 588, 598 & 590) for sterility maintenance and the B-line row was self pollinated. Paired selections were taken from paired rows 587 & 588 and 598 & 590. The F13 B-line heads and MSC6 A-line heads were harvested.

Summer 2004 Plainview, Tex. For line advancement the F13 B-line was grown in nursery row D1353 and the MSC6 B-line was grown in nursery row D1354. The B-line was crossed onto the A-line for sterility maintenance and the B-line row was self pollination. A paired selection was made and the F14 B-line and the MSC7 A-line were harvested. Additionally to generate a Foundation Increase of seed, multiple rows of the F13 B-line and MSC6 A-line were grown in nursery rows D203-214. The B-lines were crossed onto the A-line and bulk seed of the B-line and A-line was harvested to send to production.

Summer 2005 at Lubbock, Tex. For line advancement, multiple rows of the F14 B-line and the MSC7 A-line were grown in nursery rows C611-632. The B-lines were crossed onto the A-lines and the B-line was selfed. Paired selections were made and the F15 B-line and the MSC8 A-line were harvested. The bulk B-line and A-line seed from 2004 was grown in Dumas, Tex. in a Seedstock Increase block. The production group from that point forward has maintained and increased the B-line and A-line.

Spring 2006 at Bishop, Tex. The F15 B-line and the MSC8 A-line were coded and finished as GSV415986.

In an embodiment, the invention relates to *sorghum* plants having all or essentially all of the physiological and morphological characteristics of the inbred *sorghum* variety GSV415986. In an embodiment, the physiological and morphological characteristics of the inbred *sorghum* variety are set forth in Table 1. *Sorghum* variety GSV415986 has shown acceptable levels of uniformity and stability, within the limits of environmental influence, for the traits described in Table 1. *Sorghum* variety GSV415986 has been self-pollinated and head-rowed a sufficient number of generations to ensure homozygosity and phenotypic stability. In certain categories of variety description information, GSV415986 has been compared to *sorghum* varieties TX2737 and OK11.

TABLE 1

Physiological and Morphological Characteristics for *Sorghum* Variety GSV415986 and Comparative Check Varieties

| | CHARACTERISTIC | GSV415986 | TX2737 | OK11 |
|---|---|---|---|---|
| 1.A. | STALK | | | |
| | Plant Height (in.) | 38 | 51.3 | 43.7 |
| | Head Exsertion | 3.0 | 4.7 | 3.7 |
| | Anthocyanin Presence | yes | Yes | Yes |
| | Tillering | 7 | 5.7 | 5.0 |
| 1.B. | LEAF | | | |
| | Color | Medium | Medium Dark | Medium Light |
| | Length (in.) | 21 | 25 | 24.5 |
| | Width (in.) | 2.5 | 2.5 | 3 |
| | No. per Stalk. | 10 | 11 | 12 |
| | Mid Rib Color (e.g. cloudy) | Cloudy | Cloudy | Cloudy |
| | Color Pattern (e.g. solid) | Solid | Solid | Solid |
| | Attitude | SE | E | SE |
| 1.C. | HEAD | | | |
| | Panicle Type | SC | SC | SO |
| | Panicle Shape | C | C | E |
| | Panicle Length (in.) | 6.5 | 12.5 | 12 |
| | Panicle Branch Attitude | E | E | SE |
| | Panicle Branch Length (in.) | 2.25 | 2.25 | 3 |
| | Grain Set Under Bags | 0% | >95% | 0%* |
| | Panicle Blasting Percent | 0% | 0% | 3% |
| 1.D. | GRAIN | | | |
| | Glume Color | Black | Tan | Purple |
| | Awns (e.g. present or absent) | Present | Absent | Absent |
| | Seeds per Pound | 19,759 | 15,564 | 12,720 |
| | Grain Color | Red | Yellow | White |
| | Testweight (lbs per bu) | 61 | 60.1 | 59.1 |
| | Endosperm Color | White | White | White |
| | Endosperm Texture | Intermediate | Vitreous | Intermediate |
| | Threshability | 3 | 2 | 3 |
| | Grain Weathering Resistance | 2 | 4 | 4 |
| 1.E. | DISEASE TOLERANCE | | | |
| | Downy Mildew - pathotype 1 | na | 9.0 | 9.0 |
| | Downy Mildew - pathotype 3 | 9 | 9.0 | 9.0 |
| | Downy Mildew - pathotype 6 | 9.0 | 9.0 | 9.0 |
| | Maize Dwarf Mosaic Virus "A" | na | na | na |
| | Head Smut - Race 1 | 2.0 | 4.0 | 5.0 |
| | Charcoal Rot | 3.0 | 3.0 | 2.0 |
| | *Fusarium* Head Blight | 3.0 | 4.0 | 6.0 |
| 1.F. | INSECT RESISTANCE | | | |
| | Greenbug Biotype E | na | na | na |
| | Greenbug Biotype I | na | na | na |
| | Chinch Bug | na | na | na |
| | *Sorghum* Midge | 9.0 | 9.0 | 9.0 |
| 1.G. | PLANT GROWTH | | | |
| | Seedling Vigor | 4.4 | 5.0 | 6.3 |
| | Plant Color | Purple | Purple | Purple |
| | Staygreen | 4.0 | 3.0 | 2.0 |
| | Height Uniformity | 4.0 | 3.3 | 2.7 |
| | Root Lodging | 2.0 | 3.0 | 3.0 |
| | Pre-Flower Stress Tolerance | 5.0 | 2.0 | 3.0 |
| | Post-Flower Stress Tolerance | 3.0 | 3.0 | 2.0 |
| | Post-Freeze Standability | 4.0 | 3.0 | 3.0 |
| | Yield Under Stress | 5.0 | 2.0 | 3.0 |
| | Chemical Burn Resistance | na | na | na |
| | Bloom 10% | 76 | 70.8 | 82.0 |
| | Bloom 50% | 77.0 | 73.7 | 84.2 |
| | Bloom 90% | 80 | 76.5 | 86.8 |
| | Agronomic Rating | 4.0 | 2.8 | 3.3 |

**These are typical values. Values may vary due to environment.

In an embodiment, the GSV415986 *sorghum* plants of the invention are inbred. Inbred GSV415986 *sorghum* plants can be produced by planting the seeds of the inbred *sorghum* plant designated GSV415986 and growing the resulting *sorghum* plants under self-pollinating or sib-pollinating conditions with adequate isolation, using standard techniques well known to an artisan skilled in the agricultural arts.

In a particular embodiment, the present invention provides a method of producing an inbred *sorghum* plant derived from the *sorghum* variety designated GSV415986, the method comprising the steps of: (a) preparing a progeny plant derived from *sorghum* variety GSV415986, wherein said preparing comprises crossing a plant of the *sorghum* variety GSV415986 with a second *sorghum* plant; (b) crossing the progeny plant with itself or a second plant to produce a seed of a progeny plant of a subsequent generation; (c) growing a progeny plant of a subsequent generation from said seed of a progeny plant of a subsequent generation and crossing the progeny plant of a subsequent generation with itself or a second plant; and (d) repeating the steps for an additional 3 to 10 generations to produce an inbred *sorghum* plant derived from the *sorghum* variety GSV415986. In the method, it may be desirable to select particular plants resulting from step (c) for continued crossing according to steps (b) and (c). By selecting plants having one or more desirable traits, an inbred *sorghum* plant derived from the *sorghum* variety GSV415986 may be obtained which possesses some or essentially all of the desirable traits of *sorghum* variety GSV415986 as well as potentially other selected traits. In a particular embodiment, the invention comprises an elite GSV415986 *sorghum* parent plant or line.

In yet another embodiment, the invention is directed to parts of the GSV415986 *sorghum* plant. Any part of the GSV415986 *sorghum* plant is contemplated in this embodiment. In an embodiment, the plant part may comprise pollen obtained from a GSV415986 *sorghum* plant. In still another embodiment, the invention comprises seed of the GSV415986 *sorghum* plant. Seeds can be harvested from a GSV415986 plant using standard, well-known procedures.

In an embodiment, the seeds are inbred GSV415986 seeds. Inbred *sorghum* seed of the invention may be provided as an essentially homogeneous population of inbred *sorghum* seed of the variety designated GSV415986. Essentially homogeneous populations of inbred seed may be free from substantial numbers of seeds that are significantly different on a genetic basis. In an embodiment of the present invention, inbred seed may form greater than about 97% of the total seed. In an embodiment, the population of inbred *sorghum* seed of the invention may be essentially free from hybrid seed. In some embodiments, the inbred seed population may be grown separately from any hybrid population to provide an essentially homogeneous population of inbred sorghum plants designated GSV415986.

In yet another embodiment of the invention, a tissue culture of regenerable cells of a plant of the variety designated GSV415986 is provided. The regenerable cells in such tissue cultures may be derived from embryos, meristematic cells, microspores, pollen, anthers, stigma, flowers, leaves, stalks, roots, root tips, seeds, or from callus or protoplasts derived from those tissues. Means for preparing and maintaining plant tissue cultures are well known in the art.

In an embodiment, the tissue culture may be capable of regenerating plants capable of expressing essentially all of the physiological and morphological characteristics of the GSV415986 variety, and of regenerating plants having substantially the same genotype as other plants of the GSV415986 variety. Still further, the present invention provides sorghum plants regenerated from the tissue cultures of the invention, the plants having all or essentially all of the physiological and morphological characteristics of the variety designated GSV415986.

In a particular embodiment, the invention relates to a sorghum hybrid containing the sorghum variety GSV415986. A sorghum hybrid is the cross of two inbred lines, each of which may have one or more desirable characteristics lacked by the other and/or which complement the other. As used herein, crossing can include selfing, backcrossing, crossing to another or the same inbred, crossing to populations, and the like.

In an embodiment, the sorghum plants can be crossed by either natural or mechanical techniques. Natural pollination occurs in sorghum when wind blows pollen from the anthers to receptive stigmata on the same or another plant. Mechanical pollination can be effected either by controlling the types of pollen that can blow onto the receptive stigmata or by pollinating by hand. These techniques are well known in the art.

Because sorghum is normally a self-pollinated plant and because both male and female flowers are in the same panicle, a cytoplasmic male sterile (CMS) inbred may be used to produce large quantities of hybrid seed. Cytoplasmic-male sterility is a pollen abortion phenomenon determined by the interaction between the genes in the cytoplasm and the nucleus. Alteration in the mitochondrial genome and the lack of restorer genes in the nucleus will lead to pollen abortion. With either a normal cytoplasm or the presence of restorer gene(s) in the nucleus, the plant will produce pollen normally. A CMS plant can be pollinated by a maintainer version of the same variety, which has a normal cytoplasm but lacks the restorer gene(s) in the nucleus, and will continue to be male sterile in the next generation. The male fertility of a CMS plant can be restored in the subsequent generation by crossing it with a plant that contains the restorer gene(s) in the nucleus. With the restorer gene(s) in the nucleus, the offspring of the male-sterile plant can produce normal pollen grains and propagate. Thus, in a hybrid seed production system, flowers of a CMS inbred (non-restorer female parent) may be fertilized with pollen from a fertile inbred (restorer male parent) carrying genes which restore male fertility in the hybrid ($F_1$) progeny.

The development of a sorghum hybrid, in an embodiment, may involve the following steps: (1) the formation of "restorer" and "non-restorer" germplasm pools; (2) the selection of superior plants from various "restorer" and "non-restorer" germplasm pools; (3) the selfing of the superior plants for one or more generations to produce a series of inbred lines, which although different from each other, breed true and are highly uniform; (4) the conversion of inbred lines classified as females or non-restorers to CMS forms; and (5) crossing the selected CMS female inbred lines with selected fertile male inbred lines to produce the hybrid progeny ($F_1$).

In another embodiment, the development of a sorghum hybrid may involve the steps of: (1) planting in pollinating proximity seeds of a first and second parent sorghum plant (the first and second plant may be distinct inbred plants); (2) cultivating or growing the seeds of the first and second parent sorghum plants into plants that bear flowers; (3) emasculating the flowers of either the first or second parent sorghum plant, i.e. physically removing the anthers from the florets prior to blooming of the flowers so as to prevent pollen production or preventing dehiscence of pollen from anthers by introduction and maintenance of a high humidity environment by bagging a panicle or portion of a panicle with a plastic bag prior to blooming (a "wet pollination emasculation") or by using as the female parent a male sterile plant, thereby providing an emasculated parent sorghum plant; (4) allowing natural cross-pollination to occur between the first and second parent sorghum plants or mechanically moving pollen from the pollen parent to the pollen sterile seed parent; (5) harvesting seeds produced on the emasculated parent sorghum plant; and, where desired, (6) growing the harvested seed into a sorghum plant, which may be a hybrid sorghum plant.

In one embodiment, the sorghum hybrid containing the variety GSV415986 is a single cross hybrid. A single cross sorghum hybrid is the cross of two inbred plants, each of which has a genotype that complements the genotype of the other. In this embodiment, the $F_1$ hybrid may be more vigorous than its inbred parents. This hybrid vigor, or heterosis, may be manifested in many polygenic traits, including markedly improved yields, better stalks, better roots, better uniformity and better insect and disease resistance.

In an embodiment of the invention, either the first or second parent sorghum plants can be from variety GSV415986. Thus, any sorghum plant produced using sorghum plant GSV415986 forms a part of the invention. In an embodiment, the parent sorghum plants may be of different varieties. In still another embodiment, the invention comprises an elite hybrid containing the GSV415986 sorghum plant or line.

Sorghum lines are known to those of skill in the art, any one of which could be crossed with sorghum plant GSV415986 to produce a hybrid plant. The hybrid containing the GSV415986 sorghum plant of the invention may be an $F_1$ hybrid, an $F_2$ hybrid, an $F_3$ hybrid, an $F_4$ hybrid, an $F_5$ hybrid, an $F_6$ hybrid, an $F_7$ hybrid, or any further generation hybrid.

An example of an $F_1$ hybrid which has been produced with GSV415986 as a parent is the hybrid 7B30. Hybrid 7B30 was produced by crossing inbred sorghum plant GSV415986 with the inbred sorghum plant designated GSV672338.

TABLE 2

Physiological and Morphological Characteristics of a Sorghum Hybrid 7B30 Containing Sorghum Variety GSV415986

| | CHARACTERISTIC | VALUE |
|---|---|---|
| 1. | STALK | |
| | Plant Height (in.) | 55 |
| | Tillering | 8 |
| | Head Exsertion | 6 |
| | Plant Color | Purple |
| 2. | LEAF | |
| | Length (in.) | 26 |
| | Width (in.) | 2.5 |
| | Midrib Color | Cloudy |
| | Leaf Attitude | SE |

TABLE 2-continued

Physiological and Morphological Characteristics of a *Sorghum* Hybrid 7B30 Containing *Sorghum* Variety GSV415986

| CHARACTERISTIC | | VALUE |
|---|---|---|
| 3. | PANICLE | |
| | Length (in.) | 9.25 |
| | Panicle Branch Length (in.) | 3 |
| | Anther Color | Yellow |
| | Glume Color | Black |
| | Panicle Type | SO |
| | Panicle Diameter | 2.5 |
| | Awns (present or absent) | Present |
| | Panicle Appearance Rating | 3 |
| 4. | GRAIN | |
| | Endosperm Texture | Intermediate |
| | Endosperm Color | White |
| | Grain Color | Bronze |
| | Color Intensity Score | 5 |
| | Seeds Per Pound | 16,755 |

Examples of comparative data for 7B30 are set forth in Table 3, which presents a comparison of performance data for a hybrid made with GSV415986 as one parent, versus selected commercial hybrids. All the data in Table 3 represents results across years and locations for research and/or strip trials.

TABLE 3

Comparative Data for 7B30, a Hybrid Having GSV415986 as One Inbred Parent

| HYBRID | YLD | MST | STL | RTL | BLM | PUR | AGR | GSB | SVR | PHT | TWT | THR |
|---|---|---|---|---|---|---|---|---|---|---|---|---|
| 7B30 | 6,373.50 | 14 | 0 | 0 | 69 | 3.4 | 4.1 | 9 | 3.8 | 46 | 58.4 | 3 |
| DKS49-45 | 6,389.30 | 13.8 | 1 | 0 | 69 | 3.4 | 3.9 | 9 | 3.5 | 50 | 57.9 | 5.1 |
| DIFFERENTIAL | −15.8 | 0.2 | −0.9 | 0.1 | 0.0 | 0.0 | 0.3 | 0.0 | 0.3 | −3.4 | 0.5 | −2.0 |
| SIGNIFICANCE LEVEL | | * | | * | | | ** | | | ** | * | ** |
| 7B30 | 6,246.40 | 14.1 | 0 | 0 | 69 | 3.5 | 4.1 | 9 | 3.8 | 46 | 58.2 | 3.1 |
| 6B10 | 5,482.00 | 13.8 | 0 | 0 | 65 | 2.6 | 4.1 | 9 | 3.8 | 43 | 57.2 | 3.8 |
| DIFFERENTIAL | 764.5 | 0.3 | −0.2 | 0.1 | 3.5 | 0.9 | 0.0 | 0.0 | 0.0 | 2.9 | 1.0 | −0.8 |
| SIGNIFICANCE LEVEL. | ** | ** | | | ** | * | | | | ** | ** | |
| 7B30 | 6,194.20 | 14 | 0 | 0 | 69 | 3.4 | 4.1 | 9 | 3.8 | 47 | 58.5 | 2.9 |
| 7B11 | 5,660.80 | 14.1 | 0 | 0 | 69 | 3.6 | 4.4 | 9 | 5.2 | 48 | 59.4 | 2.4 |
| DIFFERENTIAL | 533.4 | 0.0 | 0.1 | 0.0 | −0.3 | −0.2 | −0.3 | 0.0 | −1.3 | −1.1 | −0.9 | 0.5 |
| SIGNIFICANCE LEVEL | ** | | | | | | ** | | | ** | ** | |

| ABBREVIATIONS LEGEND | | | |
|---|---|---|---|
| Abbreviation | Meaning | Abbreviation | Meaning |
| AGR | Agronomic Rating | PUR | Plant Uniformity Rating |
| BLM | Bloom 50% | RTL | Root Lodging (%) |
| FNSC | Final Stand Count (actual count) | SGR | Staygreen Rating |
| GSB | Grain Set under Bags | SI | Selection Index (% of check) |
| MST | Moisture at harvest (%) | STL | Stock Lodging (%) |
| na | Not Available | SVR | Seedling Vigor Rating |
| ns | Not Significant | THR | Threshability Rating |
| PHT | Plant Height (inches) | TWT | Test Weight (pounds) |
| PSR | Pollen Shed Rating | YLD | Yield (bushels/acre) |

Significance levels are indicated as:
+ = 10%,
* = 5%,
** = 1% somal location. In one embodiment of the invention, a plant of *sorghum* variety GSV415986 comprising a single locus conversion in particular is provided. In specific embodiments of the invention, an added genetic locus confers one or more additional traits. The traits conferred may include, but are not limited to, male sterility, male fertility, herbicide tolerance or resistance, insect tolerance or resistance, disease tolerance or resistance, fungal tolerance or resistance, waxy starch, enhanced nutritional quality, modified phytic acid metabolism, modified carbohydrate metabolism and modified protein metabolism.

In an embodiment, the trait may be cytoplasmically-inherited and may be passed to progeny through the female parent in a particular cross. An exemplary cytoplasmically-inherited trait is the male sterility trait. A cytoplasmically-inherited trait may be a naturally-occurring *sorghum* trait or a trait introduced through genetic transformation techniques.

In other embodiments, the trait may be conferred by a naturally-occurring *sorghum* gene introduced into the genome of the variety designated GSV415986 by backcrossing, a natural or induced mutation, or a transgene introduced through genetic transformation techniques. If backcrossing is used in an embodiment, essentially all of the desired morphological and physiological characteristics of a variety may be recovered in addition to a genetic locus transferred into the plant via the backcrossing technique.

In another embodiment of the invention, a plant of *sorghum* variety designated GSV415986 comprising an added heritable trait is provided. The heritable trait may comprise a genetic locus that is a dominant or recessive allele. When introduced through transformation, a genetic locus may comprise one or more transgenes integrated at a single chromosomal location.

In a backcross procedure, the parental *sorghum* plant which contributes the locus or loci for the desired trait is typically termed the non-recurrent or donor parent. This terminology refers to the fact that the non-recurrent parent is used one time in the backcross protocol and, therefore, does not reoccur.

The parental *sorghum* plant to which the locus or loci from the non-recurrent parent are transferred is known as the recurrent parent, as it is used for several rounds in the backcrossing protocol. In a typical backcross protocol, the original parent of interest (recurrent parent) is crossed to a second variety (non-recurrent parent) that carries the genetic locus of interest to be transferred. The resulting progeny from this cross are then crossed again to the recurrent parent and the process is repeated until a *sorghum* plant is obtained wherein essentially all of the desired morphological and physiological characteristics of the recurrent parent are recovered in the converted plant, in addition to the transferred locus from the non-recurrent parent. The backcross process may be accelerated by the use of genetic markers, such as single sequence repeat (SSR), restriction fragment length polymorphism (RFLP), single nucleotide polymorphism (SNP) or amplified fragment length polymorphism (AFLP) markers to identify plants with the greatest genetic complement from the recurrent parent.

The selection of a suitable recurrent parent is an important step for a successful backcrossing procedure. The choice of the particular non-recurrent parent will depend on the purpose of the backcross. One of the major purposes is to add commercially desirable, agronomically important traits to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine which progeny carry the desired allele.

As part of the invention, direct selection may be applied where a genetic locus acts as a dominant trait. An example of a dominant trait may be a herbicide resistance trait, which, in some cases, is inherited in a dominant fashion. For this selection process, the progeny of the initial cross may be sprayed with the herbicide prior to the backcrossing. The spraying eliminates any plants which do not have the desired herbicide resistance characteristic, and only those plants that have the herbicide resistance gene are used in the subsequent backcross. This process is then repeated for all additional backcross generations.

It will be understood by those of skill in the art that a transgene need not be directly transformed into a GSV415986 plant, as techniques for the production of stably transformed *sorghum* plants that pass single loci to progeny by Mendelian inheritance are known in the art. Such loci may, therefore, be passed from parent plant to progeny plants by standard plant breeding techniques that are well known in the art. Examples of traits that may be introduced into a GSV415986 *sorghum* plant according to the invention are provided below.

A. Male Sterility

In an embodiment, a male sterility trait is introduced into a GSV415986 *sorghum* plant. Any gene conferring male sterility may be utilized in this embodiment. In a particular embodiment, the male sterility gene may be herbicide-inducible. Male sterility genes may increase the efficiency with which hybrids are made, in that they eliminate the need to physically emasculate the *sorghum* plant used as a female in a given cross.

Where the employment of male-sterility systems is desired with a *sorghum* plant in accordance with the invention, it may be beneficial to also utilize one or more male-fertility restorer genes. For example, where CMS is used, hybrid seed production requires three inbred lines: (1) a CMS female parent line having a CMS cytoplasm and possessing no restorer genes (also known as an "A" line); (2) a fertile inbred with normal cytoplasm that possesses no restorer genes, which is isogenic with the CMS line for nuclear genes (also known as a "maintainer line" or "B line"); and (3) a distinct, fertile, male parent line with normal cytoplasm, carrying fertility restorer genes (also known as the "restorer line" or "R line"). The CMS female parent line is propagated by pollination with the maintainer line, with all of the progeny being male sterile, as the CMS cytoplasm is derived from the female parent. These male sterile plants can then be employed as the female parent in hybrid crosses with the male restorer parent, without the need for physical emasculation of the male reproductive parts of the female parent.

The presence of a male-fertility restorer gene in the male parent results in the production of fully fertile $F_1$ hybrid progeny. If no restorer gene is present in the male parent, male-sterile hybrids are obtained. Such hybrids are useful where the vegetative tissue of the *sorghum* plant is utilized, e.g., for silage, but in most cases, the seeds will be deemed the most valuable portion of the crop. In these cases, fertility of the hybrids in these crops must be restored. Therefore, one aspect of the current invention concerns plants of the *sorghum* variety GSV415986 comprising a genetic locus capable of restoring male fertility in an otherwise male-sterile plant. Examples of male-sterility genes and corresponding restorers which could be employed with the plants of the invention are known to those of skill in the art of plant breeding.

B. Herbicide Resistance or Tolerance

In an embodiment, a herbicide resistance or tolerance trait is introduced into a GSV415986 *sorghum* plant. Any gene conferring herbicide resistance or tolerance may be utilized in this embodiment. In an embodiment, the herbicide resistance or tolerance is for glyphosate, sulfonylurea, imidazalinone, dicamba, glufosinate, phenoxy proprionic acid, cycloshexone, triazine, benzonitrile, broxynil, quizalofop, nicosulfuron, acetolactate synthase-inhibiting herbicides, or 1-aminocyclopropane-1-carboxylic acid-inhibiting herbicides. Numerous herbicide resistance genes are known and may be employed with the invention.

C. Waxy Starch

In an embodiment, a waxy starch trait is introduced into a GSV415986 *sorghum* plant. Any gene conferring waxy starch characteristics may be utilized in this embodiment. The waxy characteristic is an example of a recessive trait. In this example, the progeny resulting from the first backcross generation (BC1) may be grown and selfed. A test may then be run on the selfed seed from the BC1 plant to determine which BC1 plants carried the recessive gene for the waxy trait.

D. Disease Resistance or Tolerance

In an embodiment, a disease resistance or tolerance trait is introduced into a GSV415986 *sorghum* plant. Any gene conferring disease resistance or tolerance may be utilized in this embodiment. In an embodiment, the gene may confer disease resistance to downy mildew, pathotypes 1, 3, or 6; maize dwarf mosaic virus "A"; head smut, race 1; charcoal rot; or *fusarium* head blight. In an embodiment, the disease may be a viral disease.

E. Insect Resistance or Tolerance

In an embodiment, an insect resistance or tolerance trait is introduced into a GSV415986 *sorghum* plant. Any gene conferring insect resistance or tolerance may be utilized in this embodiment. In an embodiment, such gene may confer resistance to greenbug, biotype C, E, or I; chinch bug; or *sorghum* midge.

F. Modified Phytate and Carbohydrate Metabolism

In an embodiment, a trait that confers modified phytate or carbohydrate metabolism is introduced into a GSV415986 *sorghum* plant. Any gene conferring modified phytate or carbohydrate metabolism may be utilized in this embodiment. For example, phytate metabolism may be modified by introduction of a phytase-encoding gene to enhance breakdown of phytate, adding more free phosphate to the transformed plant. A number of genes that may be used to alter carbohydrate metabolism are well known in the art.

G. Origin and Breeding History of an Exemplary Introduced Trait

GSV548413 A is a conversion of GSV548413 to cytoplasmic male sterility. GSV548413 A was derived using backcross methods. GSV548413 (a proprietary inbred of Monsanto Company) was used as the recurrent parent and GSV160919, a germplasm source carrying A1 cytoplasmic sterility, was used as the non-recurrent parent. The breeding history of the converted inbred GSV548413 A can be summarized as follows:

| | |
|---|---|
| Plainview, TX Nurseries 2003 | Made up MSCO: Female row 03 10 41 41 TXPLROY__00047__00029; Male row 03 10 41 41 TXPLROY__00013__00033 |
| Plainview, TX Nurseries 2004 | MSCO was grown and plants selected for recurrent parent type were backcrossed by GSV548413 B (rows 04 05 41 41 TXLUNURA__00039__00077 X 04 05 41 41 TXLUNURA__00039__00078) |
| Plainview, TX Nurseries 2005 | MSC1 was grown and plants selected for recurrent parent type were backcrossed by GSV548413 B (rows 05 05 41 41 TXLUNURA__00023__00092 X 05 05 41 41 TXLUNURA__00023__00093) |
| Mt. Hope, KS Nurseries 2007 | MSC2 was grown and plants selected for recurrent parent type were backcrossed by GSV548413B (rows 07 04 92 92 KSMH3B__00010__00017 X 07 04 92 92 KSMH3B__00010__00018) |
| San Juan de Abajo, MX Nurseries 2007-2008 | MSC3 was grown and plants selected for recurrent parent type were backcrossed by GSV548413B (rows 07 12 92 92 JAPV3__00037__00023 X 07 12 92 92 JAPV3__00037__00024) |
| Mt. Hope, KS Nurseries 2008 | MSC4 was grown and plants selected for recurrent parent type were backcrossed by GSV548413B (rows 08 04 92 92 KSMH4A__00063__00027 X 08 04 92 92 KSMH4A__00063__00028) |
| San Juan de Abajo, MX Nurseries 2008-2009 | MSC5 was grown and plants selected for recurrent parent type were backcrossed by GSV548413B (rows 08 12 92 92 JAPV2A__00046__00001 X 08 12 92 92 JAPV2A__00046__00002) |
| Mt. Hope, KS Nurseries 2009 | MSC6 was grown and plants were bulk crossed by GSV548413B to generate approximately one pound of seed (rows 09 04 92 92 KSMH1__00017__00001 X 09 04 92 92 KSMH1__00017__00002) |
| Villa Hidalgo, MX Nurseries 2009-2010 | MSC7 was grown and plants were bulk crossed by GSV548413B to generate approximately 30 pounds of seed for pilot and seedstock production in 2010 (rows 09 12 92 92 JAPVBLK1__00027__00057 to 09 12 92 92 JAPVBLK1__00027__00062 and 09 12 92 92 JAPVBLK1__00028__00037 to 09 12 92 92 JAPVBLK1__00028__00060 in paired rows) |

H. Illustrative Procedures for Introduction of a Desired Trait

As described above, techniques for the production of *sorghum* plants with added traits are known in the art. An example of such a procedure for preparation of a *sorghum* plant of GSV415986 comprising an added trait is as follows:

(a) crossing *sorghum* plant GSV415986 to a second (non-recurrent) *sorghum* plant comprising a locus to be converted in *sorghum* plant GSV415986;
(b) selecting at least a first progeny plant resulting from the crossing and comprising the locus;
(c) crossing the selected progeny to *sorghum* plant GSV415986; and
(d) repeating steps (b) and (c) until a plant of variety GSV415986 is obtained comprising the locus.

Following these steps, essentially any locus may be introduced into *sorghum* variety GSV415986. For example, molecular techniques allow introduction of any given locus, without the need for phenotypic screening of progeny during the backcrossing steps. Polymerase chain reaction (PCR) and Southern hybridization are two examples of molecular techniques that may be used for confirmation of the presence of a given locus and thus conversion of that locus.

The present invention additionally provides, in an embodiment, processes of preparing GSV415986 *sorghum* plants. In accordance with such an embodiment, a first parent *sorghum* plant may be crossed with a second parent *sorghum* plant wherein at least one of the first and second *sorghum* plants is the inbred *sorghum* plant GSV415986. One application of the process is in the production of $F_1$ hybrid plants. Another important aspect of this process is that it can be used for the development of novel inbred lines. For example, the inbred *sorghum* plant GSV415986 could be crossed to any second plant and the resulting hybrid progeny each selfed for about 5 to 7 or more generations, thereby providing a large number of distinct, pure-breeding inbred lines. These inbred lines could then be crossed with other inbred or non-inbred lines and the resulting hybrid progeny analyzed for beneficial characteristics. In this way, novel inbred lines conferring desirable characteristics could be identified. After at least five or more generations, the inbred plant is typically considered genetically pure. Thus, in an embodiment, the invention comprises genetically pure inbred lines produced from the inbred *sorghum* plant GSV415986.

In a particular embodiment of the invention, the genetic complement of the *sorghum* plant variety designated GSV415986 is provided. A genetic complement represents the genetic make up of an inbred cell, tissue or plant. A hybrid genetic complement represents the genetic make up of a hybrid cell, tissue or plant. The invention thus provides *sorghum* plant cells that have a genetic complement in accordance with the inbred *sorghum* plant cells disclosed herein, and plants, seeds and diploid plants containing such cells.

In still another embodiment, the present invention provides hybrid genetic complements, as represented by *sorghum* plant cells, tissues, plants, and seeds, formed by the combination of a haploid genetic complement of an inbred *sorghum* plant of the invention with a haploid genetic complement of a second *sorghum* plant, which may be another, distinct inbred *sorghum* plant. In another aspect, the present invention provides a *sorghum* plant regenerated from a tissue culture that comprises a hybrid genetic complement of this invention.

Plant genetic complements may be assessed by genetic marker profiles, and by the expression of phenotypic traits that are characteristic of the expression of the genetic complement, e.g., isozyme typing profiles. It is understood that the *sorghum* variety designated GSV415986 could be identified by any of the many known techniques such as, for example, Simple Sequence Length Polymorphisms, Randomly Amplified Polymorphic DNAs, DNA Amplification Fingerprinting, Sequence Characterized Amplified Regions, Arbitrary Primed Polymerase Chain Reaction, AFLPs, and SNPs.

A genetic marker profile of an inbred may be predictive of the agronomic traits of a hybrid produced using that inbred. For example, if an inbred of known genetic marker profile and phenotype is crossed with a second inbred of known genetic marker profile and phenotype it is possible to predict the phenotype of the $F_1$ hybrid based on the combined genetic marker profiles of the parent inbreds. Methods for prediction of hybrid performance from genetic marker data are known in the art. Such predictions may be made using any suitable genetic marker, for example, SSRs, RFLPs, AFLPs, SNPs, or isozymes.

SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by PCR, thereby eliminating the need for labor-intensive Southern hybridization. PCR detection is conducted using two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology. Following amplification, markers can be scored by gel electrophoresis of the amplification products. Scoring of marker genotype is based on the size (number of base pairs) of the amplified segment.

In another embodiment of the invention, the method relates to the production of a GSV415986 *sorghum* plant product. The *sorghum* plant product may be selected from the group consisting of starch, syrup, protein, or any other product known in the art to be made from *sorghum* plants or plant parts.

Applicant has made a deposit of at least 2,500 seeds of *sorghum* variety designated GSV415986 with the American Type Culture Collection (ATCC), 10801 University Boulevard, Manassas, Va. 20110-2209 USA, which was assigned ATCC Accession number PTA-121843. The seeds were deposited with the ATCC on Dec. 11, 2014, and were taken from a deposit maintained by Monsanto Company since prior to the filing date of this application. Access to this deposit will be available during the pendency of the application to the Commissioner of Patents and Trademarks and persons determined by the Commissioner to be entitled thereto upon request. The deposit will be maintained in the ATCC depository, which is a public depository, for a period of 30 years, or 5 years after the most recent request, or for the enforceable life of the patent, whichever is longer, and will be replaced if it becomes nonviable during that period. Applicant does not waive any infringement of its rights granted under this patent or under the Plant Variety Protection Act (7 U.S.C. 2321, et seq.).

All references cited in this specification, including without limitation, all papers, publications, patents, patent applications, presentations, texts, reports, manuscripts, brochures, books, internet postings, journal articles, and/or periodicals are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and is not intended to limit the invention so further described in such appended claims. Therefore, the spirit and scope of the appended claims should not be limited to the description of the versions contained therein.

What is claimed is:

1. A seed of *sorghum* variety GSV415986, a representative sample of seed of said *sorghum* variety GSV415986 having been deposited under ATCC Accession No. PTA-121843.

2. A *sorghum* plant, or a part thereof, produced by growing the seed of claim 1.

3. The plant part of claim 2, further defined as pollen, an ovule or a cell.

4. A tissue culture of regenerable cells of the plant of claim 2.

5. The tissue culture of claim 4, wherein the regenerable cells are produced from a plant part selected from the group consisting of embryos, meristematic cells, pollen, leaves, roots, root tips, anthers, pistils, flowers, seeds, and stalks.

6. A plant regenerated from the tissue culture of claim 4, wherein the plant comprises all of the physiological and morphological characteristics of *sorghum* variety GSV415986 listed in Table 1 as determined at the 5% significance level for quantitative data.

7. A method of producing a *sorghum* seed, comprising crossing two *sorghum* plants and harvesting the resultant *sorghum* seed, wherein at least one of the *sorghum* plants is the *sorghum* plant of claim 2.

8. A *sorghum* seed produced by the method of claim 7.

9. A *sorghum* plant, or a part thereof, produced by growing the seed of claim 8, wherein the part thereof is selected from the group consisting of embryos, meristematic cells, leaves, roots, root tips, anthers, pistils, flowers, and stalks.

10. A method of producing a plant of variety GSV415986, a representative sample of seed of said *sorghum* variety GSV415986 having been deposited under ATCC Accession No. PTA-121843, comprising an added desired trait, the method comprising introducing a transgene conferring the desired trait into a plant of variety GSV415986.

11. The method of claim 10, wherein the desired trait is selected from the group consisting of male sterility, male fertility, herbicide tolerance or resistance, insect tolerance or resistance, disease tolerance or resistance, fungal tolerance or resistance, waxy starch, enhanced nutritional quality, modified phytic acid metabolism, modified carbohydrate metabolism and modified protein metabolism.

12. The method of claim 11, wherein the desired trait is herbicide tolerance and the tolerance conferred is to an herbicide selected from the group consisting of glyphosate, sulfonylurea, imidazalinone, dicamba, glufosinate, phenoxy proprionic acid, cyclohexone, triazine, benzonitrile, broxynil, quizalofop, nicosulfuron, acetolactate synthase-inhibiting herbicides, and 1-aminocyclopropane-1-carboxylic acid-inhibiting herbicides.

13. A plant produced by the method of claim 10, wherein the plant comprises the desired trait and otherwise comprises essentially all of the physiological and morphological characteristics of variety GSV415986 listed in Table 1 as determined at the 5% significance level for quantitative data.

14. A method of introducing a single locus conversion into variety GSV415986 comprising:

(a) crossing a plant of variety GSV415986, a representative sample of seed of said *sorghum* variety GSV415986 having been deposited under ATCC Accession No. PTA-121843, with a second plant comprising a desired single locus to produce F$_1$ progeny plants;

(b) selecting one or more F$_1$ progeny plants that have the single locus;

(c) crossing the one or more selected F$_1$ progeny plants with at least a first plant of variety GSV415986 to produce backcross progeny plants;

(d) selecting backcross progeny plants that have the single locus and essentially all of the physiological and morphological characteristics of variety GSV415986 listed in Table 1 as determined at the 5% significance level for quantitative data; and (e) repeating steps (c) and (d) one or more times in succession to produce selected second or higher backcross progeny plants that comprise the single locus and essentially all of the physiological and morphological characteristics of sorghum variety GSV415986 listed in Table 1 as determined at the 5% significance level for quantitative data.

15. The method of claim 14, wherein the single locus confers a trait selected from the group consisting of male sterility, male fertility, herbicide tolerance or resistance, insect tolerance or resistance, disease tolerance or resistance, fungal tolerance or resistance, waxy starch, enhanced nutritional quality, modified phytic acid metabolism, modified carbohydrate metabolism and modified protein metabolism.

16. The method of claim 15, wherein the trait is tolerance to an herbicide selected from the group consisting of glyphosate, sulfonylurea, imidazalinone, dicamba, glufosinate, phenoxy proprionic acid, cycloshexone, triazine, benzonitrile, broxynil, quizalofop, nicosulfuron, acetolactate synthase-inhibiting herbicides, and 1-aminocyclopropane-1-carboxylic acid-inhibiting herbicides.

17. A plant of variety GSV415986, a representative sample of seed of said *sorghum* variety GSV415986 having been deposited under ATCC Accession No. PTA-121843, further defined as comprising a single locus conversion, wherein the converted plant otherwise comprises essentially all of the physiological and morphological characteristics of variety GSV415986 listed in Table 1 as determined at the 5% significance level for quantitative data.

18. A method of producing an inbred plant derived from the variety GSV415986, the method comprising the steps of:

(a) preparing a progeny plant derived from *sorghum* variety GSV415986, a representative sample of seed of said *sorghum* variety GSV415986 having been deposited under ATCC Accession No. PTA-121843, by crossing a plant of the variety GSV415986 with a plant of a second variety;

(b) crossing the progeny plant with itself or a second plant to produce a seed of a progeny plant of a subsequent generation;

(c) growing a progeny plant of a subsequent generation from said seed and crossing the progeny plant of a subsequent generation with itself or a second plant; and (d) repeating the crossing step and the growing step for an additional three or more generations with sufficient inbreeding to produce an inbred plant derived from the variety GSV415986.

19. A method of producing a plant product comprising obtaining the plant of claim 2, or a part thereof, and producing said plant product therefrom.

20. The method of claim 19, wherein the plant product is selected from the group consisting of starch, syrup and protein.

* * * * *